(12) United States Patent
Moss et al.

(10) Patent No.: US 7,494,813 B2
(45) Date of Patent: Feb. 24, 2009

(54) VAC-BAC SHUTTLE VECTOR SYSTEM

(75) Inventors: Bernard Moss, Bethesda, MD (US); Arban Domi, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 453 days.

(21) Appl. No.: 10/959,392

(22) Filed: Oct. 5, 2004

(65) Prior Publication Data

US 2005/0124070 A1 Jun. 9, 2005

Related U.S. Application Data

(63) Continuation of application No. PCT/US03/11183, filed on Apr. 10, 2003.

(60) Provisional application No. 60/402,824, filed on Aug. 9, 2002, provisional application No. 60/371,840, filed on Apr. 10, 2002.

(51) Int. Cl.
| | |
|---|---|
| C12N 15/10 | (2006.01) |
| C12N 15/63 | (2006.01) |
| C12N 15/64 | (2006.01) |
| C12N 15/70 | (2006.01) |
| C12N 15/863 | (2006.01) |
| C12N 1/21 | (2006.01) |
| A61K 48/00 | (2006.01) |

(52) U.S. Cl. ............... 435/455; 435/320.1; 435/456; 435/457; 435/235.1; 435/239; 435/252.3; 435/252.33

(58) Field of Classification Search .............. None
See application file for complete search history.

(56) References Cited

OTHER PUBLICATIONS

Afonso et al., J. Virol., 1999, vol. 73, No. 1, pp. 533-552.*
Ahn, B.-Y. et al. 1990 "Identification of the vaccinia virus gene encoding an 18-kilodalton subunit of RNA polymerase and demonstration of a 5' poly(A) leader on its early transcript" *J. Virol.* 64:3019-3024.
Baroudy, B.M. et al. 1982 "Incompletely base-paired flip-flop terminal loops link the two DNA strands of the vaccinia virus genome into one uninterrupted polynucleotide chain" *Cell* 28:315-324.
Baroudy, B.M. et al. 1982 "Structure and replication of vaccinia virus telomeres" *Cold Spring Harbor Symp. Quant. Biol.* 47:723-729.
Borst, E.M. et al. 1999 "Cloning of the human cytomegalovirus (HCMV) genome as an infectious bacterial artificial chromosome in *Escherichia coli*: a new approach for construction of HCMV mutants" *J. Virol.* 73:8320-8329.
Delange, A.M. et al. 1986 "Replication and resolution of cloned poxvirus telomeres in vivo generates linear minichromosomes with intact viral hairpin termini" *J. Virol.* 59:249-259.
Delange, A.M. 1989 "Identification of temperature-sensitive mutants of vaccinia virus that are defective in conversion of concatemeric replicative intermediates to the mature linear DNA genome" *J. Virol.* 63:2437-2444.
Delecluse, H.J. et al. 1998 "Propagation and recovery of intact, infectious epstein-barr virus from prokaryotic to human cells." *PNAS USA* 95:8245-8250.
Domi, A. et al. 2002 "Cloning the vaccinia virus genome as a bacterial artificial chromosome in *Escherichia coli* and recovery of infectious virus in mammalian cells" *PNAS USA* 99:12415-12420.
Falkner, F.G. et al. 1990 "Transient dominant selection of recombinant vaccinia viruses" *J. Virol.* 64:3108-3111.
Hoess, R. et al. 1984 "The nature of the interaction of the P1 recombinase Cre with the recombining site *loxP*" *Cold Spring Harb. Symp. Quant. Biol.* 49:761-768.
Horsburgh, B.C. et al. 1999 "Allele replacement: an application that permits rapid manipulation of herpes simplex virus type 1 genomes" *Gene Ther.* 6:922-930.
Lee, E.C. et al. 2001 "A highly efficient *Escherichia coli*-based chromosome engineering system adapted for recombinogenic targeting and subcloning of BAC DNA" *Genomics* 73:56-65.
Luckow, V.A. et al. 1993 "Efficient generation of infectious recombinant baculoviruses by site-specific transposon-mediated insertion of foreign genes into a baculovirus genome propagated in *Escherichia coli*" *J. Virol.* 67:4566-4579.
Mackett, M. et al. 1984 "General method for production and selection of infectious vaccinia virus recombinants expressing foreign genes" *J. Virol.* 49:857-864.
Mayr, A. et al. 1966 "Attenuation of virulent fowl pox virus in tissue culture and characteristics of the attenuated virus" *Zentralbl. Veterinarmed. Reihe* B 13:1-13 (German).
Merchlinsky, M. et al. 1986 "Resolution of linear minichromosomes with hairpin ends from circular plasmids containing vaccinia virus concatemer junctions" *Cell* 45:879-884.
Merchlinsky, M. et al. 1988 "Molecular cloning and sequence of the concatemer junction from vaccinia virus replicative DNA. Viral nuclease cleavage sites in cruciform structures" *J. Mol. Biol.* 199:399-413.
Merchlinsky, M. et al. 1989 "Resolution of vaccinia virus DNA concatemer junctions requires late-gene expression" *J. Virol.* 63:1595-1603.
Merchlinsky, M. et al. 1992 "Introduction of foreign DNA into the vaccinia virus genome by in vitro ligation: recombination-independent selectable cloning vectors" *Virology* 190:522-526.
Merchlinsky, M. et al. 1997 "Construction and characterization of vaccinia direct ligation vectors" *Virology* 238:444-451.
Messerle, M. et al. 1997 "Cloning and mutagenesis of a herpesvirus genome as an infectious bacterial artificial chromosome." *PNAS USA* 94:14759-14763.
Moss, B. 1996 "Genetically engineered poxviruses for recombinant gene expression, vaccination, and safety" *PNAS USA* 93:11341-11348.
Moyer, R.W. et al. 1981 "The mechanism of cytoplasmic orthopoxvirus DNA replication" *Cell* 27:391-401.
O'Connor, M. et al. 1989 "Construction of large DNA segments in *Escherichia coli.*" *Science* 244:1307-1312.

(Continued)

*Primary Examiner*—David Guzo
(74) *Attorney, Agent, or Firm*—Townsend and Townsend and Crew LLP (57) ABSTRACT

The invention relates to a VAC-BAC shuttle vector system for creation of recombinant poxviruses from DNA cloned in a bacterial artificial chromosome.

41 Claims, 6 Drawing Sheets

OTHER PUBLICATIONS

O'Gorman, S. et al. 1997 "Protamine-Cre recombinase transgenes efficiently recombine target sequences in the male germ line of mice, but not in embryonic stem cells" *PNAS* USA 94:14602-14607.

Pennington, T.H. 1977 "Isatin-βthiosemicarbazone causes premature cessation of vaccinia virus-induced late post-replicative polypeptide synthesis." *J. Gen. Virol.* 35:567-571.

Saeki, Y. et al. 1998 "Herpes simplex virus type 1 DNA amplified as bacterial artificial chromosome in *Escherichia coli*: rescue of replication-competent virus progeny and packaging of amplicon vectors" *Hum. Gene Ther.* 9:2787-2794.

Sam, C.K. et al. 1981 "Expression of poxvirus DNA in coinfected cells and marker rescue of thermosensitive mutants by subgenomic fragments of DNA" *Ann. Virol. (Inst. Pasteur)* 132E:135-150.

Scheiflinger, F. et al. 1992 "Construction of chimeric vaccinia viruses by molecular cloning and packaging" *PNAS* USA 89:9977-9981.

Seto, J. et al. 1987 "Genetic map of the vaccinia virus *Hind*III D fragment" *Virology* 160:110-119.

Smith, E.S. et al. 2001 "Lethality-based selection of recombinant genes in mammalian cells: application to identifying tumor antigens" *Nat. Med.* 7:967-972.

Smith, G.A. et al. 1999 "Construction and transposon mutagenesis in *Escherichia coli* of a full-length infectious clone of pseudorabies virus, an alphaherpesvirus" *J. Virol.* 73:6405-6414.

Timiryasova, T.M. et al. 2001 "Construction of recombinant vaccinia viruses using PUV-inactivated virus as a helper" *BioTechniques* 31:534, 536, 538-540.

Wittek, R. et al. 1977 "*Hind*III and *Sst* I restriction sites mapped on rabbit poxvirus and vaccinia virus DNA" *J. Virol.* 23:669-678.

Woodson, B. et al. 1965 "The inhibition of vaccinia virus multiplication by isatin-βthiosemicarbazone" *PNAS* USA 54:946-953.

Given, D et al. (1979) "DNA of Epstein-Barr Virus Part 5 Direct Repeats of the Ends of Epstein-Barr Virus DNA," J Virol 30(3):852-862.

Izumi, K.M. (2001) "Identification of EBV transforming genes by recombinant EBV technology," Seminars in Cancer Biology 11:407-414.

Jacob, R.J. et al. (1979) "Anatomy of Herpes Simplex Virus DNA Part 12 Accumulation of Head-to-Tail Concatemers in Nuclei of Infected Cells and Their Role in the Generation of the Four Isomeric Arrangements of Viral DNA," J Virol 29(2):448-457.

McGregor, A. et al (2001) "Recent Advances in Herpesvirus Genetics Using Bacterial Artificial Chromosomes," Mol Genetics Metabol 72:8-14.

Supplementary European Search Report corresponding to EP 03 71 8343.

* cited by examiner

SEQUENCE LISTING

<160> NUMBER OF SEQ ID NOS: 12

<210> SEQ ID NO 1
<211> LENGTH: 69
<212> TYPE: DNA
<213> ORGANISM: Artificial Sequence
<220> FEATURE:
<223> OTHER INFORMATION: oligonucleotide

<400> SEQUENCE: 1
ataggcatgc ggccgcataa cttcgtataa tgtatgctat acgaagttat agatctggcc         60
ccgcgggga         69

<210> SEQ ID NO 2
<211> LENGTH: 69
<212> TYPE: DNA
<213> ORGANISM: Artificial Sequence
<220> FEATURE:
<223> OTHER INFORMATION: oligonucleotide

<400> SEQUENCE: 2
tccccgcggg gccagatcta taacttcgta tagcatacat tatacgaagt tatgcggccg    60
catgcctat                                                            69

<210> SEQ ID NO 3
<211> LENGTH: 46
<212> TYPE: DNA
<213> ORGANISM: Artificial Sequence
<220> FEATURE:
<223> OTHER INFORMATION: L1-SphI primer

<400> SEQUENCE: 3
acatgcatgc atgaacggcg gacatattca gttgataatc ggcccc                   46

<210> SEQ ID NO 4
<211> LENGTH: 50
<212> TYPE: DNA
<213> ORGANISM: Artificial Sequence
<220> FEATURE:
<223> OTHER INFORMATION: L2-BamHI primer

<400> SEQUENCE: 4
cgcggatccc aacaatgtct ggaaagaact gtccttcatc gatacctatc               50

<210> SEQ ID NO 5
<211> LENGTH: 47
<212> TYPE: DNA
<213> ORGANISM: Artificial Sequence
<220> FEATURE:
<223> OTHER INFORMATION: R1-BamHI primer

<400> SEQUENCE: 5
agcatggatc caattctgtg agcgtatggc aaacgaagga aaaatag                  47

<210> SEQ ID NO 6
<211> LENGTH: 40
<212> TYPE: DNA
<213> ORGANISM: Artificial Sequence
<220> FEATURE:
<223> OTHER INFORMATION: R2-SphI primer

<400> SEQUENCE: 6
ggggcatgct gagtcgatgt aacactttct acacaccgat                          40

<210> SEQ ID NO 7
<211> LENGTH: 37
<212> TYPE: DNA
<213> ORGANISM: Artificial Sequence
<220> FEATURE:
<223> OTHER INFORMATION: primer

<400> SEQUENCE: 7
tgagtcgaca tggtgagcaa gggcgaggag ctgttca                             37

<210> SEQ ID NO 8
<211> LENGTH: 57
<212> TYPE: DNA
<213> ORGANISM: Artificial Sequence 
-continued

```
<220> FEATURE:
<223> OTHER INFORMATION: primer

<400> SEQUENCE: 8
ataggcatgc ggccgcccgc ggttacttgt acagctcgtc catgccgaga gtgatcc        57

<210> SEQ ID NO 9
<211> LENGTH: 52
<212> TYPE: DNA
<213> ORGANISM: Artificial Sequence
<220> FEATURE:
<223> OTHER INFORMATION: primer

<400> SEQUENCE: 9
ataggcatgc ggccgccact aattccaaac ccaccgctt tttatagtaa gt              52

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
ataggcatgc ggccgcataa cttcgtataa tgtatg                               36

<210> SEQ ID NO 11
<211> LENGTH: 63
<212> TYPE: DNA
<213> ORGANISM: Artificial Sequence
<220> FEATURE:
<223> OTHER INFORMATION: primer

<400> SEQUENCE: 11
ccgctcgagg ccaccatgtc caatttactg accgtacacc aaaatttgcc tgcattaccg     60
gtc                                                                   63

<210> SEQ ID NO 12
<211> LENGTH: 45
<212> TYPE: DNA
<213> ORGANISM: Artificial Sequence
<220> FEATURE:
<223> OTHER INFORMATION: primer

<400> SEQUENCE: 12
tcccccgggc taatcgccat cttccagcag gcgcaccatt gcccc                     45
```

VAC-BAC SHUTTLE VECTOR SYSTEM

RELATED APPLICATIONS

This application is a continuation and claims the benefit of priority of International Application No. PCT/US2003/011183 filed Apr. 10, 2003, designating the United States of America and published in English on Oct. 23, 2003, as WO 03/087330, which claims the benefit of priority of U.S. Provisional Application No. 60/371,840 filed Apr. 10, 2002 and U.S. Provisional Application No. 60/402,824 filed Aug. 9, 2002, all of which are hereby expressly incorporated by reference in their entireties.

FIELD OF THE INVENTION

The invention relates to a VAC-BAC shuttle vector system for creation of recombinant poxviruses from DNA cloned in a bacterial artificial chromosome.

BACKGROUND OF THE INVENTION

Poxviruses, which comprise a large family of double-stranded DNA viruses that infect vertebrate and invertebrate hosts, are distinguished by their large size, complex morphology, cytoplasmic site of replication, and encoding of proteins for viral transcription, replication, and immune defense (Moss, B. 2001 in: *Fields Virology*, eds. Knipe, D. M. & Howley, P. M. Lippincott Williams & Wilkins, Philadelphia, Vol. 2, pp. 2849-2883). Vaccinia virus (VAC), the best-studied member of the poxvirus family, was used for immunization against smallpox (Fenner, F. et al. 1988 *Smallpox and its Eradication* World Health Organization, Geneva) and subsequently as an expression vector for laboratory investigations and recombinant vaccines (Moss, B. 1996 *PNAS USA* 93:11341-11348). The introduction of new genes into the VAC genome is usually carried out by homologous recombination in infected cells. Typically, a foreign gene is cloned into a plasmid transfer vector downstream of a VAC promoter and flanked by VAC DNA from a non-essential site (Mackett, M. et al 1984 *J Virol* 49:857-864). The plasmid is then transfected into cells that are infected by VAC. Because recombination is inefficient, a variety of selection and screening methods have been devised (Earl, P. L. et al. 1998 in: *Current Protocols in Molecular Biology*, eds. Ausubel, F. M. et al. Greene Publishing Associates & Wiley Interscience, New York, Vol. 2, pp. 16.17.1-16.17.19). The process usually requires three to five plaque purifications over a period of several weeks. Alternative methods, involving the purification and cleavage of the VAC genome and either ligation in vitro or three-way recombination in vivo, have been described (Merchlinsky, M. & Moss, B. 1992 *Virology* 190: 522-526; Scheiflinger, F. et al. 1992 *PNAS USA* 89:9977-9981; Merchlinsky, M. et al. 1997 *Virology* 238:444-451; Smith, E. S. et al. 2001 *Nat Med* 7:967-972; Timiryasova, T. M. et al. 2001 *Biotechniques* 31:534-540) but are cumbersome, depend on the presence of a unique restriction endonuclease site within the nearly 200,000 base pair genome, and still require plaque purification. The mutagenesis of VAC genes is even more difficult, and is usually carried out by a laborious transient dominant selection recombination scheme (Falkner, F. G. & Moss, B. 1990 *J Virol* 64:3108-3111).

Recently, the large DNA genomes of a baculovirus (Luckow, V. A. et al. 1993 *J Virol* 67:4566-4579) and several herpesviruses (Messerle, M. et al. 1997 *PNAS USA* 94:14759-14763; Borst, E. M. et al. 1999 *J Virol* 73:8320-8329; Delecluse, H. J. et al. 1998 *PNAS USA* 95:8245-8250; Horsburgh, B. C. et al. 1999 *Gene Ther* 6:922-930; Saeki, Y. et al. 1998 *Hum Gene Ther* 9:2787-2794; Smith, G. A. & Enquist, L. W. 1999 *J Virol* 73:6405-6414) have been cloned as bacterial artificial chromosomes (BACs). These circular mini-F BAC plasmids allow viral genomes to be stably maintained at low copy number and manipulated in *Escherichia coli* and then reconstituted as infectious virus by transfection of eukaryotic cells. The construction of baculovirus and herpesvirus BACs was relatively straightforward: plasmid sequences were inserted by recombination into the circular mature or replicating viral genomes and the latter were propagated in *E. coli*. Poxvirus genomes, however, are composed of linear double-stranded DNA molecules with covalently closed hairpin ends (Baroudy, B. M. et al. 1982 *Cell* 28:315-324) that are resolved from transient head-to-head or tail-to-tail concatemers during replication (Moyer, R. W. & Graves, R. L. 1981 *Cell* 27:391-401; Baroudy, B. M. et al. 1982 *Cold Spring Harbor Symp Quant Biol* 47:723-729; Merchlinsky, M. et al. 1988 *J Mol Biol* 199:399-413). Therefore, the method used for cloning baculovirus and herpesvirus genomes seemed inapplicable.

SEGUE TO THE INVENTION

Circular bacterial plasmids that contain the poxvirus concatemer junction sequence are resolved into linear minichromosomes when transfected into poxvirus-infected cells (Merchlinsky, M. & Moss, B. 1986 *Cell* 45:879-884; Delange, A. M. et al. 1986 *J Virol* 59:249-259). It seemed likely to us that a much larger plasmid containing the entire poxvirus genome and concatemer junction would also be resolved. Although it may be possible to assemble such a 200,000 bp plasmid by in vitro methods, we chose an alternative approach that depended on an observation made several years ago. It was found that poxvirus DNA concatemers accumulated under conditions in which viral late protein synthesis was specifically inhibited and that recombination occurred so that about half of the concatemers were in the head-to-tail configuration (Merchlinsky, M. & Moss, B. 1989 *J Virol* 63:1595-1603; DeLange, A. M. 1989 *J Virol* 63:2437-2444). The latter configuration was crucial because a circle formed from a head-to-tail concatemer would contain the entire genome, whereas a circle formed from head-to-head or tail-to-tail concatemers would not. In principal, head-to-tail concatemers might undergo further recombination to form circles, although the latter have not been described. Alternatively, the highly efficient bacteriophage Cre-loxP recombinase system (Hoess, R. et al. 1984 *Cold Spring Harb Symp Quant Biol* 49:761-768) could be used to specifically enhance circularization. A loxP site is composed of a 34 bp sequence consisting of a core spacer of 8 bp and two 13 bp palindromic flanking sequences. When two cis loxP sites are in the same orientation, the DNA between them can be excised and circularized by Cre. One strategy was to clone the loxP sites so that they would be in the same orientation in head-to-tail concatemers but opposite for head-to-head or tail-to-tail concatemers. Here, we describe the formation and isolation of circular plasmids containing the full length VAC genome with an intact concatemer junction sequence. These VAC-BACs were stably propagated in *E. coli* and converted into infectious virus in mammalian cells. VAC-BACs allow the generation of mutant or recombinant viral genomes in bacteria, without need for recombination or plaque purification in mammalian cells.

SUMMARY OF THE INVENTION

The invention relates to a VAC-BAC shuttle vector system for creation of recombinant poxviruses from DNA cloned in a bacterial artificial chromosome.

A VAC-BAC is a bacterial artificial chromosome (BAC) containing a vaccinia virus genome (VAC) that can replicate in bacteria and produce infectious virus in mammalian cells.

What are the uses of a VAC-BAC?
VAC-BACs can be used to modify vaccinia virus DNA by deletion, insertion or point mutation or add new DNA to the VAC genome with methods developed for bacterial plasmids, rather than by recombination in mammalian cells.
An important use is to produce recombinant vaccinia viruses for gene expression.
Other uses include the production of modified vaccinia viruses that have improved safety or immunogenicity.

What are the advantages of a VAC-BAC?
Manipulation of DNA is much simpler and faster in bacteria than in mammalian cells.
VAC-BACs are clonally purified from bacterial colonies before virus reconstitution in mammalian cells.
Modified genomes can be characterized prior to virus reconstitution.
Only virus with modified genomes will be produced so that virus plaque isolations are not needed.
Generation of a stock of virus from a VAC-BAC is accomplished within a week rather than many weeks.
Multiple viruses can be generated at the same time since plaque purification is unnecessary.

BRIEF DESCRIPTION OF THE DRAWINGS

FIG. 1. Scheme for construction of VAC-loxP-GFP-BAC. The plasmid pMBO1374-loxP was constructed by addition of a synthetic oligonucleotide containing a loxP site between the NotI and SacII sites of pMBO1374. pMBO1374-loxP-TK$_{RL}$ was derived from pMBO1374-loxP by insertion of a BamHI fragment containing the inverted halves of the TK gene, separated by a SphI site. pMBO1374-loxP-TK$_{RL}$ was then cleaved with NotI and ligated to a NotI fragment containing the VAC P7.5 promoter regulating GFP to form pMBO1374-loxP-GFP-loxP-TK$_{RL}$. The latter plasmid was cleaved with SphI to form a linear DNA flanked by the left and right halves of the TK gene, which was transfected into cells that were infected with either VAC strain WR or ts21 at 37° C. or 31° C., respectively, to allow homologous recombination. VAC-loxP-GFP-BAC was isolated by TK negative selection and plaques exhibiting green fluorescence were picked several times in succession. The recombinant virus was called WR-loxP-GFP-BAC or ts21-loxP-GFP-BAC, depending on the parental virus strain.

FIG. 3. Screening of bacterial colonies for VAC-BACs. After transformation of E. coli with DNA from cells infected with ts21-loxP-GFP-BAC in the presence of Cre, individual colonies were screened by hybridization to $^{32}$P-labeled probes containing DNA from the HindIII C and B terminal fragments of the VAC genome. Colonies number 5, 13, 16, 22, 34, 51, and 59 reacted with the C probe and, except for number 16, reacted with the B probe.

FIG. 4. The terminal HindIII C and B sequences of VAC DNA are fused in the VAC-BAC. Representations of the linear VAC genome and circular VAC-BAC DNA are shown in the upper left and right, respectively. DNA from five VAC-BAC clones and that of VAC genomic DNA were digested with HindIII, resolved by agarose gel electrophoresis, transferred to a membrane and hybridized to $^{32}$P-labeled probes containing sequences from the HindIII B or C fragment of the VAC genome. The B and C probes reacted with fragments of 30 and 22 kbp of VAC WR genomic DNA but with a 52-kbp fragment of the VAC-BACs.

FIG. 5. Detection of the concatemer junction fragment in VAC-BAC DNA. The hairpin terminus and concatemer junctions are represented in the left upper and lower portions of the figure. The sites of BstEII cleavage and the resulting size fragments are indicated. The boxes with vertical lines represent tandem repeat sequences. DNA from VAC (WR) and VAC-BAC number 5 were digested with BstEII and the products were resolved by agarose gel electrophoresis, transferred to a membrane, and probed with $^{32}$P-labeled DNA containing tandem repeat sequences located close to the two ends of the genome. An autoradiograph is shown on the right. m, is DNA size markers. The 1.3 kbp hairpin terminus was detected in WR DNA and the 2.6 kbp concatemer junction in the VAC-BAC. The upper band, in both the WR and #5 lanes, was generated by cleavage at a distal BstEII site not shown in the diagram.

FIG. 6. Size and stability of VAC-BAC DNA. (A) DNA of VAC (WR), ts21-loxP-GFP-BAC (R) and numbered VAC-BACs were analyzed by pulsed field gel electrophoresis. Similar bands (arrow) of approximately 200,000 bp were detected by ethidium bromide staining. Only a segment of the gel is shown. (B) The same DNA samples were digested with HindIII and analyzed by agarose gel electrophoresis. Note that the BC fragments of the VAC-BACs migrate with the A fragment. In addition, the J-size fragment of WR (lower arrow) is missing in ts21-loxP-GFP-BAC and all of the VAC-BACs because of inserted DNA. In VAC-BACs 5, 13, 34, and 51, the positions of the more slowly migrating J fragment containing BAC sequences is shown by the upper arrow. In ts21-loxP-GFP-BAC and VAC-BAC 22, the J fragment also contains the GFP gene and therefore migrates more slowly and coincides with the next higher band.

DETAILED DESCRIPTION OF THE PREFERRED EMBODIMENT

The ability to manipulate the vaccinia virus (VAC) genome, as a plasmid in bacteria, would greatly facilitate genetic studies and provide a powerful alternative method of making recombinant viruses. VAC, like other poxviruses, has a linear, double-stranded DNA genome with covalently closed hairpin ends that are resolved from transient head-to-head and tail-to-tail concatemers during replication in the cytoplasm of infected cells. Our strategy to construct a nearly 200,000 base pair VAC-bacterial artificial chromosome (BAC) was based on circularization of head-to-tail concatemers of VAC DNA. Cells were infected with a recombinant VAC containing inserted sequences for plasmid replication and maintenance in Escherichia coli; DNA concatemer resolution was inhibited leading to formation and accumulation of head-to-tail concatemers, in addition to the usual head-to-head and tail-to-tail forms; the concatemers were circularized by homologous or Cre-loxP mediated recombination; and E. coli were transformed with DNA from the infected cell lysates. Stable plasmids containing the entire VAC genome, with an intact concatemer junction sequence, were identified. Rescue of infectious VAC was consistently achieved by transfecting the VAC-BAC plasmids into mammalian cells that were infected with a helper non-replicating fowlpox virus.

VAC-BAC Shuttle Vectors

VAC-BAC shuttle vectors are envisioned as supplanting other methods of making genetically engineered or recombinant poxviruses, which are used in hundreds of academic and commercial laboratories. Moreover the simplicity and rapidity of the new procedure is envisioned as greatly expanding the use of poxvirus expression vectors. The VAC-BAC vector is envisioned as being modified to allow expression by vaccinia virus of foreign genes inserted into the VAC-BAC by site-specific recombination or transposition. In one embodiment, the foreign gene is envisioned as encoding a therapeutic or immunogenic gene product. In another embodiment, the therapeutic or immunogenic gene product is envisioned as being a member selected from the group consisting of a growth factor, hormone, enzyme, vaccine antigen, cytotoxin, immunomodulatory protein, antisense RNA molecule, small interfering RNA, and ribozyme. The efficiency of the system is envisioned as allowing the screening of entire cDNA libraries for use in proteomics and to identify cancer-specific CTL epitopes. In addition, because genetic engineering can be done entirely in bacteria and no selection or screening is required for isolation of recombinant viruses, the procedure is well adapted for commercial companies to make clinical grade materials under good manufacturing practices. We anticipate a commercial kit including competent *E. coli* containing the VAC-BAC shuttle vector, a donor plasmid, and a helper avian poxvirus.

A Representation Strategy for Constructing VAC-BACs

The process consisted of (i) inserting mini-F plasmid, loxP and GFP sequences into the VAC genome by homologous recombination, (ii) infecting cells with the recombinant VAC and promoting the accumulation of head-to-tail concatemers by inhibiting viral late protein synthesis (Merchlinsky, M. & Moss, B. 1989 *J Virol* 63:1595-1603; DeLange, A. M. 1989 *J Virol* 63:2437-2444) using ts21, a temperature-sensitive VAC with a mutation in the RPO18 subunit of RNA polymerase (Seto, J. et al. 1987 *Virology* 160:110-119; Ahn, B. -Y. et al. 1990 *J Virol* 64:3019-3024), or by adding isatin-β-thiosemicarbazone (IBT) (Woodson, B. & Joklik, W. K. 1965 *PNAS USA* 54:946-953; Pennington, T. H. 1977 *J Gen Virol* 35:567-571), (iii) allowing genome circularization to occur by homologous or Cre-mediated recombination, and (iv) transforming *E. coli*. The TK site was chosen for insertion of DNA sequences because it is non-essential and has been used extensively for this purpose (Mackett, M. et al. 1984 *J Virol* 49:857-864).

Using Site-specific Recombination

The terms "sequence-specific recombinase" and "site-specific recombinase" refer to enzymes that recognize and bind to a short nucleic acid site or sequence and catalyze the recombination of nucleic acid in relation to these sites.

The term "recombination site" refers to a short nucleic acid site or sequence which is recognized by a sequence- or site-specific recombinase and which become the crossover regions during the site-specific recombination event. Examples of such recombination sites include, but are not limited to, lox sites, frt sites, att sites and dif sites.

The term "lox site" as used herein refers to a nucleotide sequence at which the product of the cre gene of bacteriophage P1, Cre recombinase, can catalyze a site-specific recombination. A variety of lox sites are known to the art including the naturally occurring loxP (the sequence found in the P1 genome), loxB, loxL and loxR (these are found in the *E. coli* chromosome) as well as a number of mutant or variant lox sites such as loxP511, loxΔ86, loxΔ117, loxC2, loxP2, loxP3 and loxP23.

A variety of other site-specific recombinases may be employed in the methods of the present invention in place of the Cre recombinase. Alternative site-specific recombinases include:

1) the FLP recombinase of the 2pi plasmid of *Saccharomyces cerevisiae* (Cox 1983 *PNAS USA* 80:4223) which recognize the frt site which, like the loxP site, comprises two 13 bp inverted repeats separated by an 8 bp spacer;
2) the Int recombinase of bacteriophage lambda (with or without Xis) which recognizes att sites (Weisberg et al. 1983 In: *Lambda II*, Hendrix et al. Eds., Cold Spring Harbor Press, Cold Spring Harbor, N.Y., pp. 211-250);
3) the xerC and xerD recombinases of *E. coli* which together form a recombinase that recognizes the 28 bp dif site (Leslie and Sherratt 1995 *EMBO J* 14:1561);
4) the Int protein from the conjugative transposon Tn916 (Lu and Churchward 1994 *EMBO J* 13:1541);
5) TpnI and the β-lactamase transposons (Levesque 1990 *J Bacteriol* 172:3745);
6) the Tn3 resolvase (Flanagan et al. 1989 *J Mol Biol* 206:295 and Stark et al. 1989 *Cell* 58:779);
7) the SpoIVC recombinase of *Bacillus subtilis* (Sato et al. 1990 *J Bacteriol* 172:1092);
8) the Hin recombinase (Galsgow et al. 1989 *J Biol Chem* 264:10072);
9) the Cin recombinase (Hafter et al. 1988 *EMBO J* 7:3991); and
10) the immunoglobulin recombinases (Malynn et al. 1988 *Cell* 54:453).

Cloning of BAC Sequences into the VAC Genome

Figure 1:
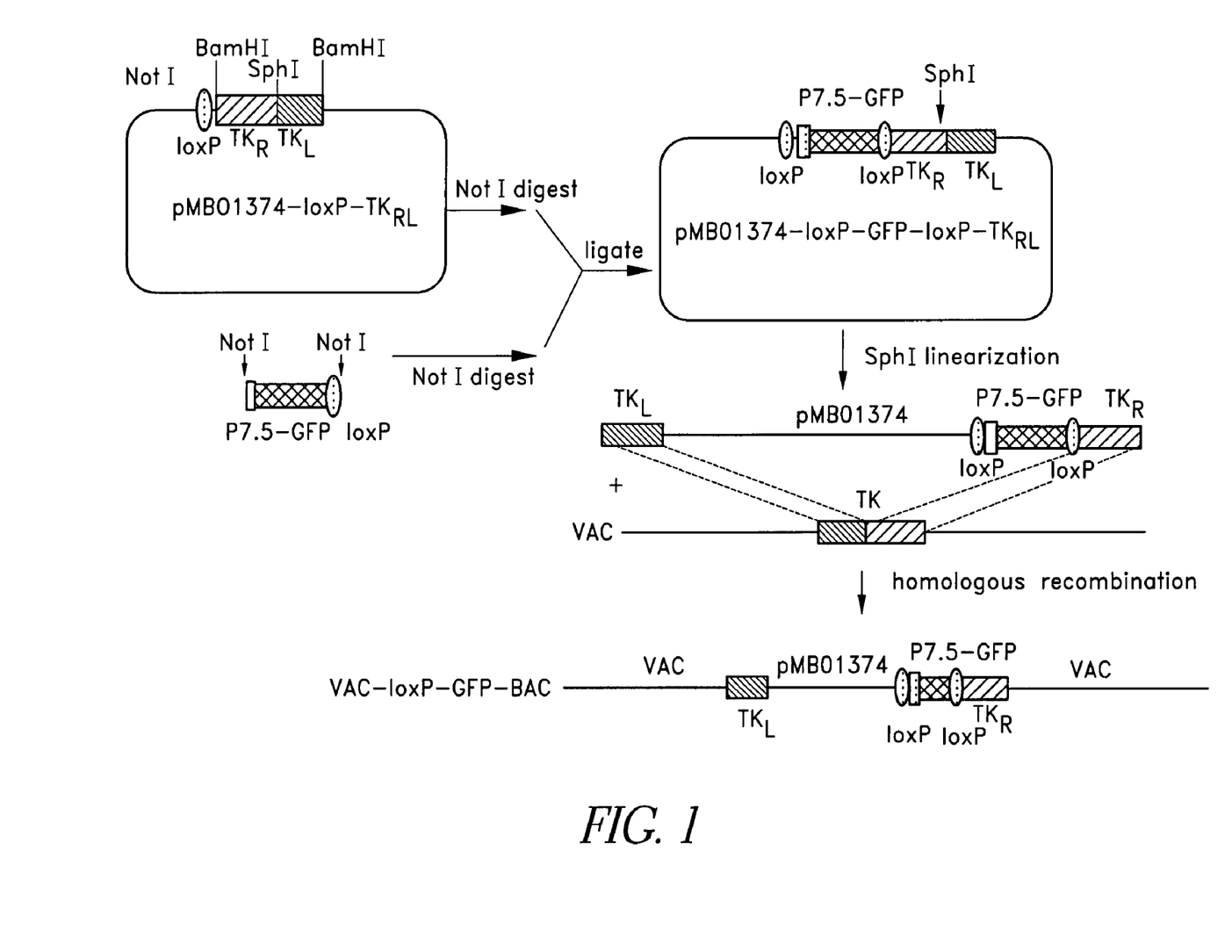

A multi-step procedure was used for construction of the plasmid transfer vector pMBO1374-loxP-GFP-loxP-TK$_{RL}$, which contains a split VAC TK ORF with the two halves in reverse orientation and a GFP expression cassette flanked by loxP sites (FIG. 1). By digesting the plasmid with SphI, a linear DNA with the TK left (TK$_L$) and TK right (TK$_R$) sequences at the two ends was produced. This DNA was transfected into cells infected with wild-type VAC strain WR or ts21 at the permissive temperature of 37 or 31° C., respectively, to allow homologous recombination (Mackett, M. et al 1984 *J Virol* 49:857-864). Recombinant virus was repeatedly purified from plaques that formed under TK$^-$ selection conditions and exhibited green fluorescence. Restriction enzyme analysis showed that the HindIII J fragment of the VAC genome, which contains the TK ORF, increased in size from about 5 kbp to 14 kbp. The insertion of DNA into the TK locus was also demonstrated by PCR. The recombinant VAC-loxP-GFP-BACs were designated WR- or ts21- depending on the parental VAC strain.

Circularization of the VAC Genome

Figure 2:
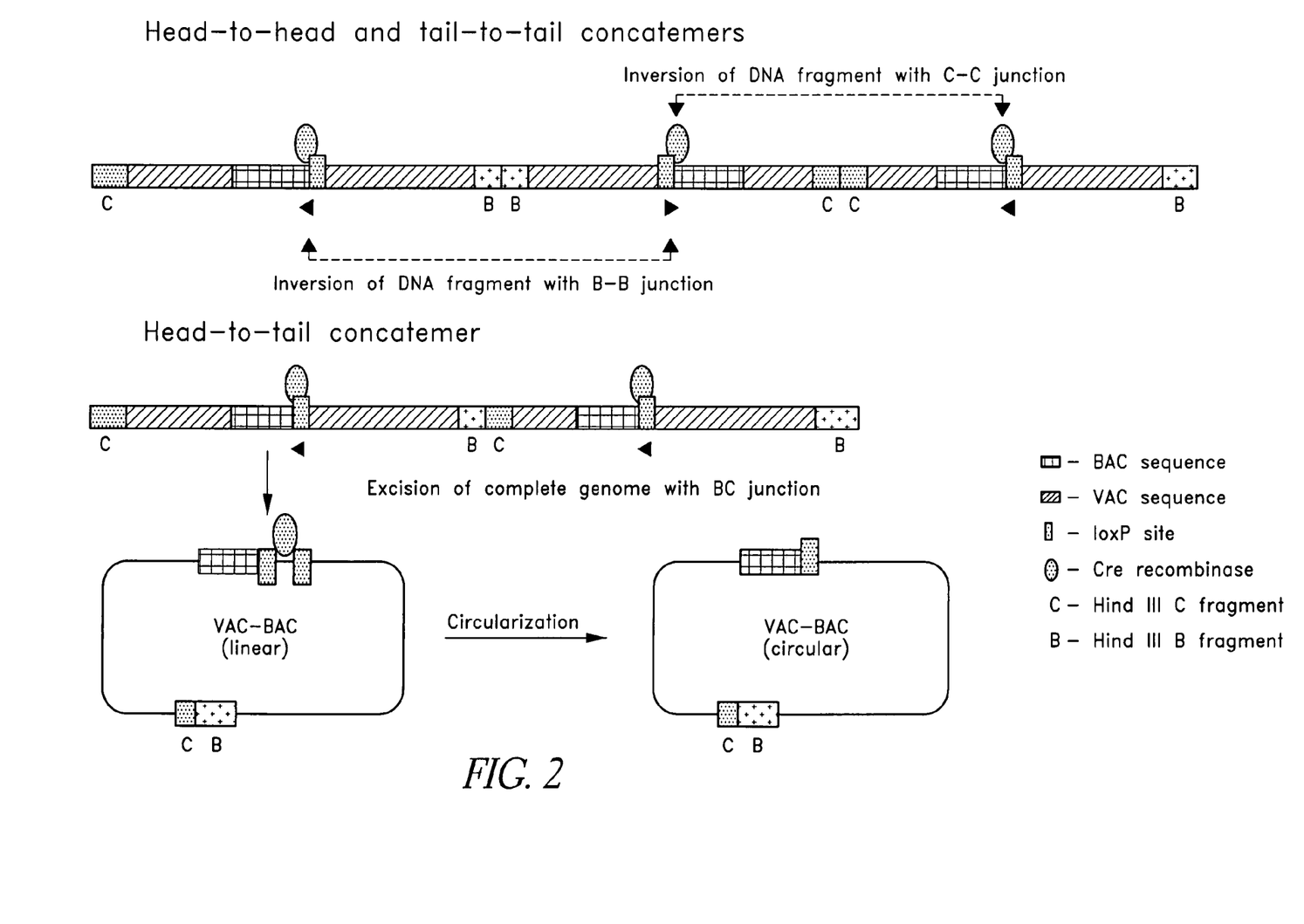
FIG. 2. Representation of the action of Cre on head-to-head, tail-to-tail, and head-to-tail concatemers. B and C represent the terminal HindIII fragments of the VAC genome. CC, BB, and CB represent head-to-head, tail-to-tail, and head-to-tail concatemer junctions, respectively. Because of the orientation of the loxP sites, excision and circularization of a complete viral genome only occurs with head-to-tail junctions.

Initial efforts to make a VAC-BAC were carried out using ts21-loxP-GFP-BAC. The accumulation of concatemeric DNA in cells infected with ts21-loxP-GFP-BAC at the non-permissive temperature of 40° C. was demonstrated by pulsed field gel electrophoresis and by detection of concatemer junctions by restriction enzyme analysis and DNA hybridization. To enhance circularization of the VAC genome, a Cre expression plasmid was transfected into cells prior to infecting them with ts21-loxP-GFP-BAC. The GFP cassette, which is flanked by similarly oriented loxP sites should be efficiently excised leaving a single loxP site in each VAC unit genome. A unit length genome flanked by loxP sites in the same orientation would also be excised from the concatemer, whereas DNA inversion would occur between oppositely oriented loxP sites. As seen in FIG. 2, loxP sites in the same orientation occur only in head-to-tail (BC) concatemers. Following excision, the DNA would be circularized by Cre to form a plasmid containing a complete VAC genome. Note that even if excision occurred with the oppositely oriented loxP sites flanking BB or CC junctions, the products would not include an entire VAC genome and would either lack BAC sequences or contain two unstable copies.

Figure 3:
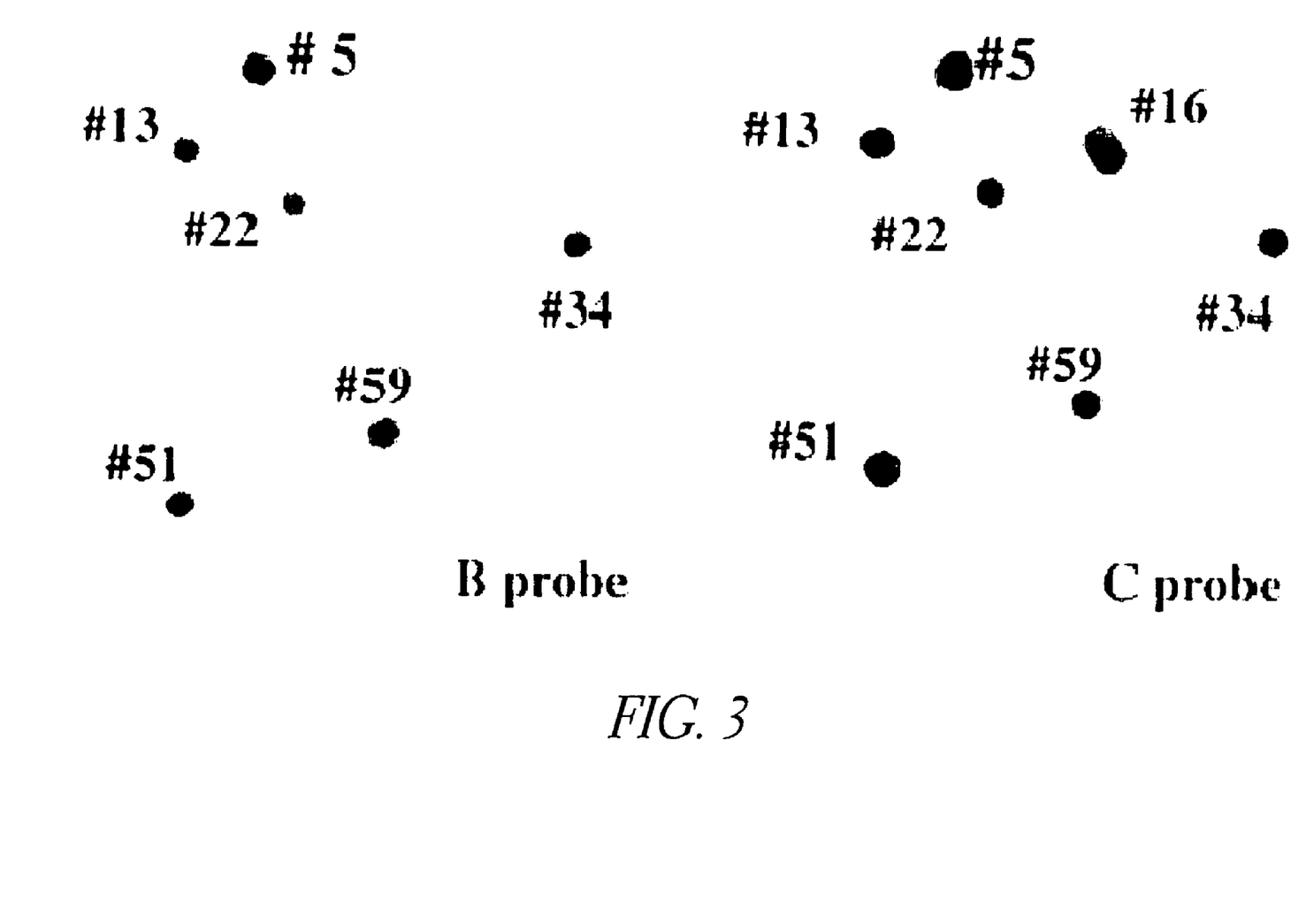

E. coli were electroporated with DNA from the lysates of cells that had been infected with ts21-loxP-GFP-BAC and then plated on chloramphenicol selective medium. Bacterial colonies were picked, transferred to duplicate membranes, and hybridized with $^{32}$P-labeled probes containing sequences from the terminal HindIII C or B fragments of the VAC genome. Of 117 colonies analyzed, DNA from six (#5, 13, 22, 34, 51, and 59) reacted with both probes, one (#16) reacted with the C probe alone, and none reacted with the B probe alone (FIG. 3). Colonies that did not react with either probe were not extensively examined, but most had relatively small fragments of VAC DNA.

Analysis of the VAC-BAC DNA

Figure 4:
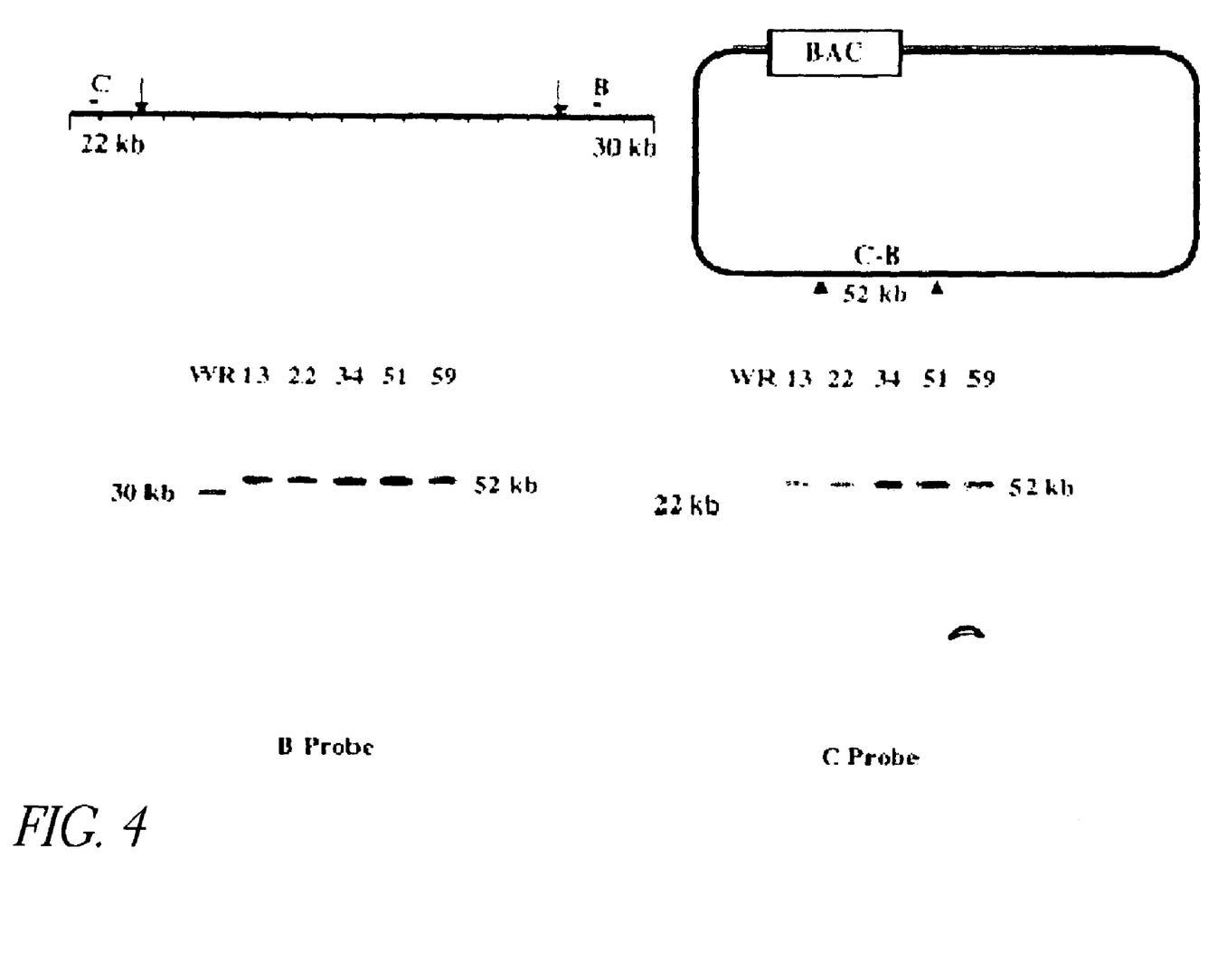

As diagrammed in FIG. 4, digestion of the linear VAC genome with HindIII should release terminal B and C fragments of 30 and 22 kbp, respectively (Wittek, R. et al. 1977 *J Virol* 23:669-678). By contrast, the HindIII C and B sequences of the circular VAC-BAC genome should be fused through the concatemer junction resulting in a combined HindIII CB fragment of 52 kbp. DNA from five VAC-BAC clones and that of authentic VAC genomic DNA were analyzed. The C and B sequences of the VAC-BAC clones were released as a single fragment of the expected size (FIG. 4).

Figure 5:
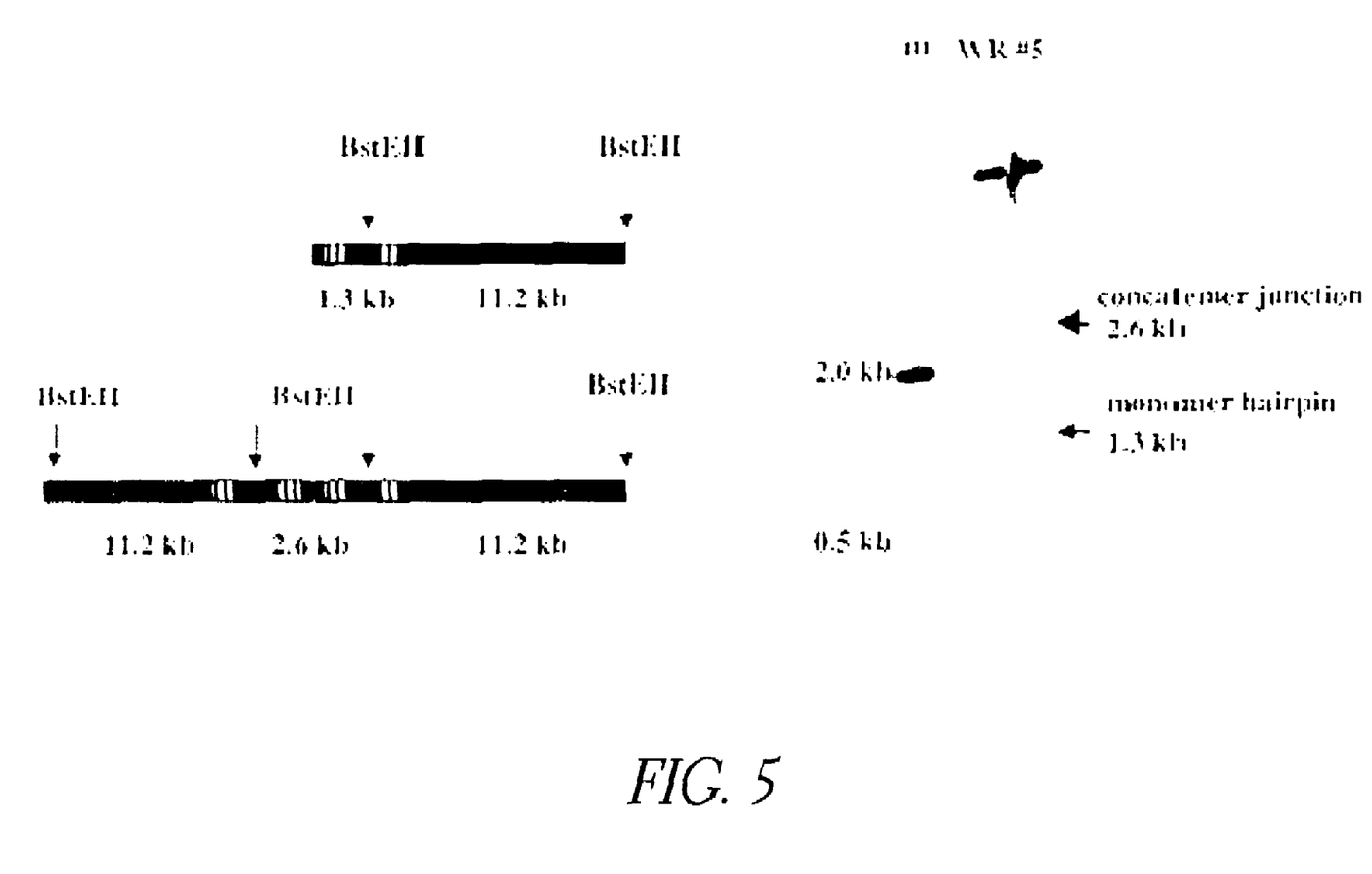

Evidence that the concatemer junction links the C and B sequences was obtained by analyzing the digestion products of BstEII, a restriction enzyme that cuts near the hairpin ends of the mature genome. As depicted in FIG. 5 (left), BstEII cleaves 1.3 kbp from the hairpin end of the mature genome or 1.3 kbp on either side of the concatemer junction. As expected, a 1.3 kbp terminal fragment was detected when WR genomic DNA was analyzed, whereas a double size 2.6 kbp junction fragment was detected from VAC-BAC DNA (FIG. 5, right).

Figure 6A:
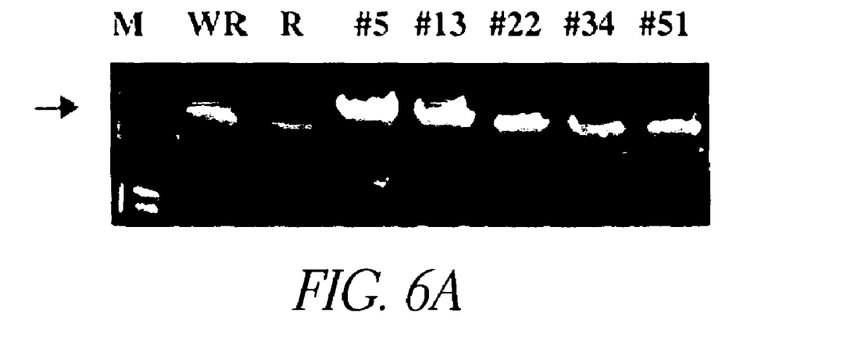

To determine whether the VAC-BACs contained full-length viral genomes, five were digested with ApaI restriction enzyme, which only cuts within the BAC sequence, and analyzed by pulsed-field gel electrophoresis. As seen in FIG. 6A, the mobilities of the cloned DNAs were similar to each other and to VAC genomic DNA.

Figure 6B:
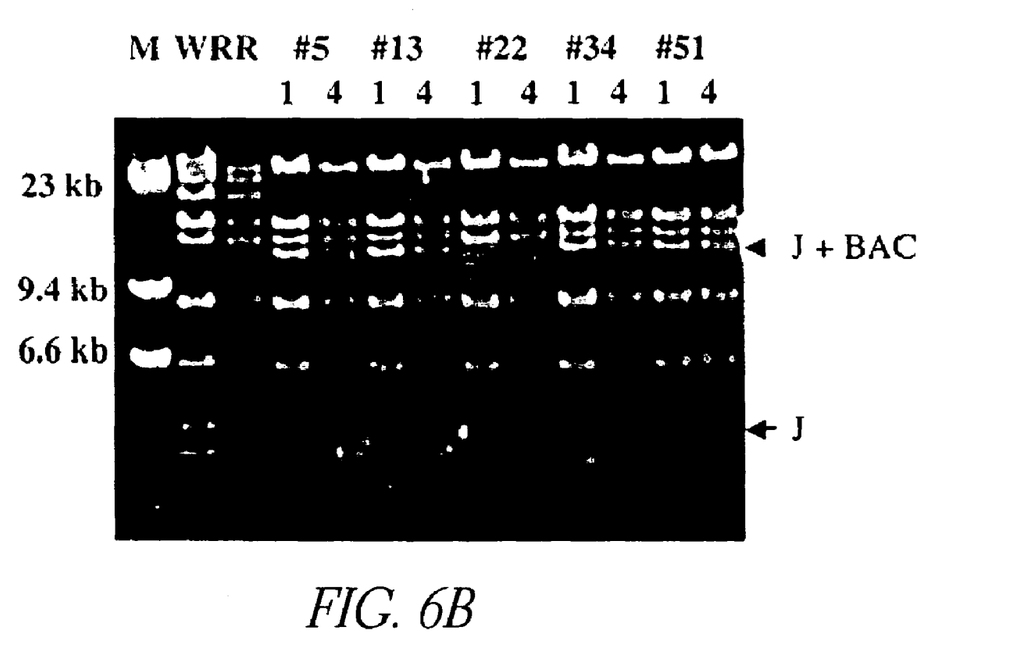

DNA stability was determined for five clones during four successive overnight cultures. The HindIII restriction patterns of DNA isolated from the first and the fourth culture were identical in each case (FIG. 6B). As expected, the 53-kbp HindIII A fragment and the 52 kbp HindIII CB junction fragment co-migrated at the top of the gel. The 12.8 kbp fragment, indicated by the upper arrow, was derived from the 5-kbp HindIII J fragment of VAC and contained BAC sequences. In clone 22 (and ts21-loxP-GFP-BAC), the corresponding fragment also contained the GFP cassette, which in this case had not been excised by Cre and therefore migrated with the next higher band of about 14 kbp. The latter result suggested that the level of Cre may have been limiting and that the efficiency of VAC-BAC formation might be improved by higher expression.

Rescue of Infectious Virus

The next step was reconstitution of infectious virus from the VAC-BACs. Poxviruses replicate and transcribe their genomes in the cytoplasm, rather than the nucleus of infected cells. To accomplish this, poxviruses encode a unique transcription system that includes a multi-subunit DNA-dependent RNA polymerase, stage-specific promoters and cognate transcription factors (Moss, B. 2001 in: *Fields Virology*, eds. Knipe, D. M. & Howley, P. M. Lippincott Williams & Wilkins, Philadelphia, Vol. 2, pp. 2849-2883). The viral RNA polymerase and early transcription factors are packaged within infectious particles in order to begin a new infection. Therefore, an infection cannot be initiated with viral DNA alone and consequently a helper virus that provides early functions must be provided. For example, rabbitpox virus was recovered from rabbitpox DNA when the transfected cells were infected with a temperature-sensitive mutant of ectromelia virus (Sam, C. K. & Dumbell, K. R. 1981 *Ann Virol* 132E:135-150). Similarly, wild-type VAC was recovered when VAC DNA was transfected into cells that were infected with a temperature-sensitive mutant of VAC (Merchlinsky, M. & Moss, B. 1992 *Virology* 190:522-526) or the genetically distant fowlpox virus, which cannot replicate in mammalian cells or undergo recombination with VAC (Scheiflinger, F. et al. 1992 *PNAS USA* 89:9977-9981).

The previous rescue experiments were done with linear viral genomes with hairpin ends. Based on studies with cloned concatemer junctions (Merchlinsky, M. & Moss, B. 1986 *Cell* 45:879-884; Delange, A. M. et al. 1986 *J Virol* 59:249-259), however, we thought that the VAC-BACs would be replicated and resolved into linear genomes. CV-1 cells were infected with a low multiplicity of fowlpox virus, transfected with VAC-BAC DNA, and incubated for 4 to 8 days at 31° C. The recovery of infectious virus was determined by plaque assay on BS-C-1 cells, which like CV-1 cells are non-permissive for fowlpox virus. Comparable amounts of infectious virus were recovered from each of the VAC-BAC clones, whereas no virus was detected when either fowlpox virus or VAC-BAC was omitted (Table 1). As expected from the analysis of the parental plasmid, virus derived from clone 22 expressed GFP. The Hind III restriction enzyme digestion patterns of the virus clones were similar to each other and no fowlpox virus DNA was detected by Southern blotting. Thus, a poxvirus genome was successfully cloned and replicated as a bacterial plasmid and rescued as infectious virus.

TABLE 1

| Rescue of infectious vaccinia virus | | |
|---|---|---|
| DNA (2 µg) | Fowlpox Virus | PFU/$10^6$ cells |
| VAC-BAC #5 | + | 675 |
| VAC-BAC #13 | + | 900 |
| VAC-BAC #22 | + | 1125 |
| VAC-BAC #51 | + | 338 |
| VAC-BAC #59 | + | 495 |

TABLE 1-continued

Rescue of infectious vaccinia virus

| DNA (2 µg) | Fowlpox Virus | PFU/10⁶ cells |
|---|---|---|
| VAC-BAC #5 | − | 0 |
| None | + | 0 |

Alternative Methods of Producing VAC-BACs

In principal, circular genomes could also arise by homologous recombination of head-tail-concatemers either in the infected cells or in the bacteria after transfection. To evaluate this possibility, cells were transfected with ts21-loxP-GFP-BAC without the Cre-expressing plasmid. Under these conditions, one of 100 plasmids analyzed contained a complete VAC genome capable of producing infectious virus.

The VAC-BACs described thus far contain the ts21 mutation. Although this mutation could be eliminated by homologous recombination, we succeeded in producing VAC-BACs starting from the wild-type WR genome. A similar strategy was employed except that isatin-β-thiosemicarbazone (IBT) was used to accumulate head-to-tail concatemers.

We also attempted to make VAC-BACs without preventing concatemer resolution, with the thought that low amounts of head-to-tail concatemers might occur naturally. Several hundred plasmid clones were analyzed and some with nearly complete genomes were identified, leading us to believe that complete genomes might be recovered after a more extensive search. Thus, while Cre-mediated recombination and inhibition of concatemer resolution increase the efficiency of VAC genome circularization, they are not essential for producing VAC-BACs.

Development of the VAC-BAC Shuttle Vector System

Poxvirus genomes consist of linear, double-stranded DNA molecules with covalently closed hairpin ends that do not undergo circularization during replication. Therefore, the straightforward method successfully used for cloning baculovirus and herpesvirus genomes as BACs (Borst, E. M. et al. 1999 *J Virol* 73:8320-8329; Delecluse, H. J. et al. 1998 *PNAS USA* 95:8245-8250; Horsburgh, B. C. et al. 1999 *Gene Ther* 6:922-930; Messerle, M. et al. 1997 *PNAS USA* 94:14759-14763; Saeki, Y. et al. 1998 *Hum Gene Ther* 9:2787-2794; Smith, G. A. and L. W. Enquist 1999 *J Virol* 73:6405-6414) was inapplicable. We knew, however, that circular bacterial plasmids that contain the poxvirus concatemer junction sequence are resolved into linear minichromosomes when transfected into poxvirus-infected cells (Delange, A. M. et al. 1986 *J Virol* 59:249-259; Merchlinsky, M. and B. Moss 1986 *Cell* 45:879-884). Therefore, we predicted that if an entire poxvirus genome were cloned as a circular plasmid with the concatemer junction sequence preserved, it would be resolved into a complete linear genome. The question, then, was how to construct such a 200,000 bp plasmid. Although it seemed possible to assemble this by in vitro methods starting with a plasmid containing a small concatemer junction, we decided on an alternative approach that depended on a curious observation made many years ago (DeLange, A. M. 1989 *J Virol* 63:2437-2444; Merchlinsky, M. and B. Moss 1989 *J Virol* 63:1595-1603). It was found that poxvirus DNA concatemers, which form as transient head-to-head and tail-to-tail genomes, accumulated under conditions in which viral late protein synthesis was inhibited (by use of specific temperature-sensitive mutants or with the drug isatin-β-thiosemicarbazone) and that the concatemers underwent recombination so that about half were in the head-to-tail configuration. This observation was crucial, because a circle formed from a head-to-tail concatemer would contain the entire genome, whereas a circle formed from head-to-head or tail-to-tail concatemers would not. The next question, then, was how to circularize the concatemer. One way would be to cleave the concatemer at a unique restriction site in vitro and ligate the ends together. However, we devised an alternative that specifically circularized head-to-tail recombinants and could be performed in vivo. This method took advantage of the efficiency and directionality of the Cre-loxP recombinase system. A loxP site is composed of a 34 bp sequence consisting of a core spacer of 8 bp and two 13 bp palindromic flanking sequences. When two cis loxP sites are in the same orientation, the DNA between them is excised and circularized; when the two sites are opposite, inversion occurs instead of excision. Our strategy then, was to clone the loxP sites so that they would be in the same orientation in head-to-tail concatemers but opposite for head-to-head or tail-to-tail concatemers. The system worked as planned and several clones containing the entire VAC genome were isolated and characterized. Importantly, the VAC-BACs were stable in *E. coli* after repeated cultures.

The next step was to reconstitute infectious virus from the VAC-BACs. Poxviruses replicate and transcribe their genomes in the cytoplasm, rather than the nucleus of infected cells. To accomplish this, poxviruses encode a unique transcription system that includes a multisubunit DNA-dependent RNA polymerase, stage-specific promoters and cognate transcription factors (Moss, B. 2001 in: D. M. Knipe and P. M. Howley (ed.), *Fields Virology* 4th ed., vol. 2 Lippincott Williams & Wilkins, Philadelphia p. 2849-2883). The viral RNA polymerase and early transcription factors are packaged within infectious particles in order to initiate a new infection. Therefore, an infection cannot be initiated with naked viral DNA. However, Sam and Dumbell (Sam, C. K., and K. R. Dumbell 1981 *Ann Virol* 132E:135-150) demonstrated that when DNA from rabbitpox virus was introduced into cells infected with a temperature-sensitive mutant of ectromelia virus, rabbitpox virus was recovered. Similarly, when VAC DNA was transfected into cells that were infected with a temperature-sensitive mutant of VAC, wild type virus was recovered (Merchlinsky, M. and B. Moss 1992 *Virology* 190: 522-526). Scheiflinger et al. (Scheiflinger, F. et al. 1992 *PNAS USA* 89:9977-998) extended this technique by demonstrating that fowlpox virus rescued VAC DNA in mammalian cells that are non-permissive for fowlpox virus. Only VAC was recovered and recombination did not occur between the fowlpox virus and VAC genomes because of their sequence diversity. Here we showed that fowlpox virus could also rescue a VAC-BAC. The procedure consists of simply infecting mammalian cells with fowlpox virus (or another poxvirus that has restricted growth in mammalian cells) and transfecting the cells with the VAC-BAC. After several days, the cells can be harvested and infectious virus recovered without need for plaque purification.

The plasmid sequences can be inserted at any non-essential site in the VAC genome. Here we used the TK locus because it has been extensively used as a recombination site, disruption does not impair virus replication in tissue culture, and homologous recombination with a TK DNA fragment could be used to remove the insert. However, disruption of the TK gene does reduce the pathogenicity of VAC (Buller, R. M. L. et al. 1985 *Nature* 317:813-815) and alternative versions of 
the VAC-BAC system can use other sites of insertion and allow substitute procedures for excision of BAC sequences.

The ability to clone and propagate the entire VAC genome as a BAC makes it possible to modify or delete VAC genes or add foreign DNA using a variety of methods developed for bacterial systems. After completion of the DNA manipulation, infectious virus can be isolated without plaque isolation, allowing high throughput procedures. We envision the procedures used to construct VAC-BACs as being applied with minor modifications to other poxviruses, African swine virus, and additional linear double-stranded genomes with hairpin termini.

General Conclusions

The ability to propagate the entire VAC genome as a BAC, makes it possible to modify or delete VAC genes or add foreign DNA using a variety of methods developed for bacterial systems (Lee, E. C. et al. 2001 *Genomics* 73:56-65). Moreover, by eliminating the need for plaque purification, production of recombinant viruses for library screening or other high throughput purposes should be facilitated.

Cells Lines and Viruses

Monolayers of BS-C-1 and CV-1 African green monkey cells, and human A543 cells were grown in Dulbecco's modified Eagle medium or Eagle minimal medium supplemented with 5 or 10% fetal calf serum (GIBCO). The VAC strain WR ts21 mutant (Seto, J. et al. 1987 *Virology* 160:110-119) was prepared by infecting confluent BS-C-1 monolayers at 31° C. with 0.01 plaque-forming units (PFU) of virus per cell. The attenuated fowlpox virus HP1.441 (Mayr, A. & Malicki, K. 1966 *Zentralbl Veterinarmed [B]* 13:1-13) was provided by G. Sutter and grown in chick embryo fibroblasts.

Plasmids

The mini-F BAC plasmid pMBO1374 (O'Connor, M. et al. 1989 *Science* 244:1307-1312), a derivative of pMBO131 (O'Gorman, S. et al. 1997 *PNAS USA* 94:14602-14607), was provided by G. A. Smith. A DNA fragment containing NotI-loxP-BglII-HaeIII-SacII sites was formed by annealing synthetic oligonucleotides 5'ataggcatGCGGCCGCATAACTTCGTATAATGTATGCTATACGAAGTTATAGATCT GGCCCCGCGGgga (SEQ ID NO: 1) and 5'tccCCGCGGGGCCAGATCTATAACTTCGTATAGCATACATTATACGAAGTTATG CGGCCGCatgcctat (SEQ ID NO: 2) (sequences in bold and lower case letters are restriction endonuclease sites and additional bases, respectively), digested with SacII and NotI, and ligated to SacII and NotI cleaved pMBO1374 resulting in pMBO1374-loxP.

Left (531 bp) and right (263 bp) segments of the vaccinia virus thymidine kinase (TK) gene were amplified by polymerase chain reaction (PCR) using the primer pairs 5'acatGCATGCATGAACGGCGGACATATTCAGTTGATAATCGGCCCC (SEQ ID NO: 3) (L1-SphI) and 5'cgcGGATCCCAACAATGTCTGGAAAGAACTGTCCTTCATCGATACCTATC (SEQ ID NO: 4) (L2-BamHI) and the primer pairs 5'agcatGGATCCAATTCTGTGAGCGTATGGCAAACGAAGGAAAAATAG (SEQ ID NO: 5) (R1-BamHI) and 5'gggGCATGCTGAGTCGATGTAACACTTTCTACACACCGAT (SEQ ID NO: 6) (R2-SphI), respectively. The two fragments were digested with SphI and ligated together to form a 543 bp DNA in which the orientation of the left and right TK segments was reversed. This $TK_{RL}$ fragment was gel purified, digested with BamHI and then ligated to BamHI-digested and shrimp alkaline phosphatase-treated pMBO1374-loxP to form pMBO1374-loxP-$TK_{RL}$ (FIG. 1).

The ORF encoding enhanced green fluorescent protein (GFP) was amplified by PCR from pEGFP-N1 (Clontech) using 5'tgaGTCGACATGGTGAGCAAGGGCGAGGAGCTGTTCA (SEQ ID NO: 7) and 5'ataggcatGCGGCCGCCCCGCGGTTACTTGTACAGCTCGTCCATGCCGAGAGTGATC C (SEQ ID NO: 8) primers, digested with SalI and NotI and gel purified. A three-way ligation was carried out with the latter fragment, the SacII and NotI digested NotI-loxP-BglII-HaeIII-SacII DNA, and SalI and NotI digested pSC11-S-B-A-K-N (Earl, P. L. et al 1998 in: *Current Protocols in Molecular Biology,* eds. Ausubel, F. M. et al. Greene Publishing Associates & Wiley Interscience, New York, Vol. 2, pp. 16.17.1-16.17.19) to form pSC11-GFP-loxP in which the VAC P7.5 promoter regulates GFP. The P7.5-GFP-loxP fragment was amplified by PCR from the latter plasmid using the primers: 5'ataggcatGCGGCCGCCACTAATTCCAAACCCACCCGCTTTTTATAGTAAGT (SEQ ID NO: 9) and 5'ataggcatGCGGCCGCATAACTTCGTATAATGTATG (SEQ ID NO: 10). The PCR product was digested with NotI and inserted in the unique NotI site of pMBO1374-loxP-$TK_{RL}$ to form pMBO1374-loxP-GFP-loxP-$TK_{RL}$ (FIG. 1), which was used to produce a recombinant VAC.

The pOG231 expression plasmid, containing Cre fused to a nuclear localization signal (O'Gorman, S. et al. 1997 *PNAS USA* 94:14602-14607), was provided by G. A. Smith. The Cre-expression cassette, excluding the nuclear localization signal, was subcloned by PCR using the following primers: 5'ccgCTCGAGGCCACCATGTCCAATTTACTGACCGTACACCAAAATTTGCCTGCATTACCGGTC (SEQ ID NO: 11) and 5'tccCCCGGGCTAATCGCCATCTTCCAGCAGGCGCACCATTGCCCC (SEQ ID NO: 12). The Cre cassette was inserted in XhoI- and SmaI-digested pCIneo (PROMEGA) to form pCI-Cre in which the Cre gene was under the control of a cytomegalovirus promoter.

All constructs were analyzed by restriction enzyme digestions and the inserted fragments and junctions were sequenced.

Construction of VAC WR- or ts21-loxP-GFP-BAC

BS-C-1 cells in a six-well plate were infected with 0.01 plaque forming units (PFU) of VAC WR or ts21 per cell. At 2 h after infection, the cells were transfected with 10 μl of LIPOFECTAMINE (Life Technology) and 2-3 μg of pMBO1374-loxP-GFP-loxP-$TK_{RL}$ that had been cut once with SphI. After 48 h at 37° C. for WR or the permissive temperature of 31° C. for the ts mutant, the cells were harvested and the virus was released by three freeze-thaw cycles. $TK^-$ recombinant VAC was selected in $TK^-$ A543 cells in the presence of 25 μg of bromodeoxyuridine per ml of medium. Plaques that exhibited green fluorescence were picked at 48 h after infection and purified by 5 cycles of plaque-isolation. The DNA of the recombinant VAC was analyzed by PCR and by digestion with the HindIII restriction enzyme.

Analysis of Concatemers by Pulsed-field Gel Electrophoresis

BS-C-1 cells in a six-well plate were infected at a multiplicity of 3 PFU of ts21 or ts21-loxP-GFP-BAC and incubated for 24 h at 31° C. or 40° C. The cells were harvested, recovered by low-speed centrifugation (1,000×g for 5 min at 4° C.) and 2 million cells were embedded per agarose plug. The DNA was extracted using CHEF Genomic DNA Plug Kit (BIO-RAD). Slices from the agarose plugs were sealed in 1% agarose and analyzed by pulsed-field electrophoresis in 1% agarose (pulsed-field certified agarose, BIO-RAD) in 0.5× TBE (BIO-RAD) at 4-5 V/cm for 20-22 h, with a switch time of 50 and 90 s.

In some experiments, the plugs were incubated with 50 units of HindIII in 0.5 ml of digestion buffer for 12 h at 37° C. The buffer was replaced with 0.5 ml of fresh digestion buffer and 50 units of HindIII for 8 h more at 37° C. After electrophoresis, the gel was stained with ethidium bromide, photographed, exposed to UV light for 5 min, transferred to a nylon membrane and hybridized to $^{32}$P labeled probes containing part of the VAC HindIII B, C or A fragment.

Isolation of Viral DNA

Infected cells from an individual well of a 6-well plate were harvested, collected by low-speed centrifugation, rinsed 2-3 times with phosphate buffered saline, suspended in 50 µl of 0.15 M NaCl-0.02 M Tris-HCl (pH 8.0)-0.01 M EDTA buffer, followed by addition of 250 µl of 0.02 M Tris-HCl (pH 8.0)-0.01 M EDTA-0.75% SDS containing 0.65 mg of proteinase K per ml. After incubation for 10-12 h at 37° C., the samples were extracted twice with 1 volume of phenol, once with phenol-chloroform and once with chloroform, precipitated with ethanol and the DNA was dissolved in 20 µl of Tris-EDTA.

Detection of Concatemer Junction Fragments

DNA was digested with BstEII, subjected to electrophoresis through a 1% agarose gel, and analyzed by Southern blotting using a $^{32}$P-labeled probe containing the terminal 70 bp repeat sequence.

Cre-loxP Recombination and Transformation of E. coli

BS-C-1 cells in individual wells of a six-well plate were transfected with 2 µg of pCI-Cre and 10 µl of LIPO-FECTAMINE (Life Technology) and incubated at 37° C. At 24 h after transfection, the cells were infected with 5 PFU per cell of ts21-loxP-GFP-BAC and incubated for 24 h at 40° C. Alternatively, cells were infected with WR-loxP-GFP-BAC and incubated at 37° C. in the presence of 45 µM of isatin-β-thiosemicarbazone (IBT) per ml. The cells were harvested by scraping and DNA was extracted as described above, dissolved in 20 µl of Tris-EDTA, and used to transform E. coli DH10B electrocompetent cells (GIBCO BRL) in 0.1 cm cuvettes with the Gene Pulser electroporation system (BIO-RAD) at 1.8 kV, 200Ω and 25 µF. Bacteria were recovered in 1 ml of SOC medium (GIBCO) at 37° C. for 1 h, plated on LB-agar containing 50 µg of chloramphenicol and incubated overnight at 37° C. DNA was isolated by the alkaline lysis method and in some cases was purified by polyethylene glycol precipitation.

Rescue of Infectious Virus

CV-1 cells in a 12-well plate were infected with fowlpox virus (0.005 PFU per cell), transfected with 2 µg of VAC-BAC DNA, and incubated for 4 to 8 days at 31° C.

Modified BAC without Terminal Poxvirus Genome Sequences

In some circumstances, it may be advantageous to construct a BAC without the DNA sequences corresponding to the ends of the poxvirus genome. One way in which this can be accomplished is by constructing a recombinant poxvirus that has sequences for plasmid replication in E. coli in a non-essential site and a lox site introduced near each end of the poxvirus genome. Cells that express the Cre recombinase are infected with the recombinant poxvirus and the DNA is isolated and used to transfect E. coli. The circular BAC will then lack the concatemer junction sequence. Therefore, a helper plasmid is also constructed that contains the concatemer junction and additional flanking sequences. The procedure for making the infectious poxvirus using a helper non-replicating virus is then modified by co-transfecting the helper plasmid and the VAC-BAC into mammalian cells where homologous recombination between sequences of the helper plasmid and VAC-BAC can occur. When appropriately designed, the lox sites will be removed during the recombination.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A bacterial artificial chromosome (BAC) comprising a viral genome in a circular form with a head-to-tail concatemer junction and sequences for plasmid replication in *E. coli* inserted in the viral genome in a non-essential site, wherein said viral genome is the genome of a vaccinia virus.

2. The BAC of claim 1, wherein said viral genome is modified by deletion, insertion, or point mutation, or to add a foreign gene.

3. A method of making the BAC of claim 1, comprising at ers to occur by site-directed recombination, wherein said viral genome is the genome of a vaccinia virus.

6. A method of making the BAC of claim 1, comprising at least:
infecting cells with a recombinant virus, having a viral genome in which sequences for a lox site and plasmid replication in *E. coli* are inserted in the viral genome in a non-essential site, under conditions that allow genome circularization of head-to-tail concatemers to occur by Cre-mediated recombination, wherein said viral genome is the genome of a vaccinia virus.

7. A method of making the BAC of claim 1, comprising at least:
(a) providing a recombinant virus having a viral genome in which sequences for plasmid replication in *E. coli* are inserted in the viral genome in a non-essential site;
(b) infecting cells with the recombinant virus under conditions that promote the accumulation of head-to-tail concatemers; and (c) allowing genome circularization of head-to-tail concatemers to occur, wherein said viral genome is the genome of a vaccinia virus.

8. A method of making the BAC of claim 1, comprising at least:
(a) providing a recombinant virus having a viral genome in which sequences for plasmid replication in *E. coli* are inserted in the viral genome in a non-essential site;
(b) infecting cells with the recombinant virus under conditions that promote the accumulation of head-to-tail concatemers; and
(c) allowing genome circularization of head-to-tail concatemers to occur by homologous recombination, wherein said viral genome is the genome of a vaccinia virus.

9. A method of making the BAC of claim 1, comprising at least:
(a) providing a recombinant virus having a viral genome in which sequences for a recombination site and plasmid replication in *E. coli* are inserted in the viral genome in a non-essential site;
(b) infecting cells with the recombinant virus under conditions that promote the accumulation of head-to-tail concatemers; and
(c) allowing genome circularization of head-to-tail concatemers to occur by site-directed recombination, wherein said viral genome is the genome of a vaccinia virus.

10. A method of making the BAC of claim 1, comprising at least:
(a) providing a recombinant virus having a viral genome in which sequences for a lox site and plasmid replication in *E. coli* are inserted in the viral genome in a non-essential site;
(b) infecting cells with the recombinant virus under conditions that promote the accumulation of head-to-tail concatemers; and
(c) allowing genome circularization of head-to-tail concatemers to occur by Cre-mediated recombination, wherein said viral genome is the genome of a vaccinia virus.

11. A method of making the BAC of claim 1, comprising at least:
(a) infecting cells with a recombinant virus, having a viral genome in which sequences for plasmid replication in *E. coli* are inserted in the viral genome in a non-essential site, under conditions that promote the accumulation of head-to-tail concatemers; and (b) allowing genome circularization of head-to-tail concatemers to occur, wherein said viral genome is the genome of a vaccinia virus.

12. A method of making the BAC of claim 1, comprising at least:
(a) infecting cells with a recombinant virus, having a viral genome in which sequences for plasmid replication in *E. coli* are inserted in the viral genome in a non-essential site, under conditions that promote the accumulation of head-to-tail concatemers; and
(b) allowing genome circularization of head-to-tail concatemers to occur by homologous recombination, wherein said viral genome is the genome of a vaccinia virus.

13. A method of making the BAC of claim 1, comprising at least:
(a) infecting cells with a recombinant virus, having a viral genome in which sequences for a recombination site and plasmid replication in *E. coli* are inserted in the viral genome in a non-essential site, under conditions that promote the accumulation of head-to-tail concatemers; and
(b) allowing genome circularization of head-to-tail concatemers to occur by site-directed recombination, wherein said viral genome is the genome of a vaccinia virus.

14. A method of making the BAC of claim 1, comprising at least:
(a) infecting cells with a recombinant virus, having a viral genome in which sequences for a lox site and plasmid replication in *E. coli* are inserted in the viral genome in a non-essential site, under conditions that promote the accumulation of head-to-tail concatemers; and
(b) allowing genome circularization of head-to-tail concatemers to occur by Cre-mediated recombination, wherein said viral genome is the genome of a vaccinia virus.

15. A method of propagating BAC comprising transforming competent *E. coli* with the BAC of claim 1.

16. A method of manipulating DNA to produce an infectious virus comprising modifying or deleting viral genes or adding foreign DNA to the BAC of claim 1.

17. A method of rescuing infectious virus comprising transfecting the BAC of claim 1 into mammalian cells that are infected with a helper non-replicating virus.

18. A kit comprising competent *E. coli* comprising the BAC of claim 1, a donor plasmid, and a helper non-replicating virus.

19. Competent *E. coli* comprising the BAC of claim 1.

20. The BAC of claim 2, wherein said foreign gene encodes a therapeutic or immunogenic gene product.

21. The BAC of claim 20, wherein said therapeutic or immunogenic gene product is a member selected from the group consisting of a growth factor, hormone, enzyme, vaccine antigen, cytotoxin, immunomodulatory protein, antisense RNA molecule, small interfering RNA, and ribozyme.

22. The method of any of claims 3-14 wherein the conditions that allow genome circularization of head-to-tail concatemers to occur or that promote the accumulation of head-to-tail concatemers comprise inhibiting concatemer resolution by adding isatin-β-thiosemicarbazone (IBT).

23. The method of any of claims 3-14 wherein the conditions that allow genome circularization of head-to-tail concatemers to occur or that promote the accumulation of head- 24. The method of any of claims 3-14 further comprising recovering said BAC.

25. The method of any claims 3-14 further comprising transforming competent *E. coli* with the BAC.

26. The method of any of claims 3-14 further comprising modifying or deleting viral genes or adding foreign DNA to the BAC.

27. The method of any of claims 3-14 further comprising rescuing infectious virus by transfecting the BAC into mammalian cells that are infected with a helper non-replicating virus.

28. An infectious virus produced by the method of claim 16.

29. The method of claim 17 wherein the helper non-replicating virus is a poxvirus.

30. The method of claim 29 wherein the poxvirus is an avian poxvirus.

31. The method of claim 30 wherein the avian poxvirus is a fowlpox virus.

32. The kit of claim 18 wherein the helper non-replicating virus is a poxvirus.

33. The kit of claim 32 wherein the poxvirus is an avian poxvirus.

34. The kit of claim 33 wherein the avian poxvirus is a fowlpox virus.

35. A bacterial artificial chromosome (BAC) comprising a viral genome, lacking the terminal sequences, in a circular form and sequences for plasmid replication in *E. coli* inserted in the viral genome in a non-essential site, wherein said viral genome is the genome of a vaccinia virus.

36. The BAC of claim 35, wherein said viral genome is modified by deletion, insertion, or point mutation, or to add a foreign gene.

37. A method of making the BAC of claim 35, comprising at least:
(a) providing a recombinant virus having a viral genome in which sequences for plasmid replication in *E. coli* are inserted in the viral genome in a non-essential site and in which recombination sites are inserted near the ends of the genomes;
(b) infecting cells with the recombinant virus; and
(c) allowing deletion of the ends of the genome and circularization to occur by site-directed recombination, wherein said viral genome is the genome of a vaccinia virus.

38. A method of making the BAC of claim 35, comprising at least:
(a) providing a recombinant virus having a viral genome in which sequences for plasmid replication in *E. coli* are inserted in the viral genome in a non-essential site and in which lox sites are inserted near the ends of the genomes;
(b) infecting cells with the recombinant virus; and
(c) allowing deletion of the ends of the genome and circularization to occur by Cre-mediated recombination, wherein said viral genome is the genome of a vaccinia virus.

39. A method of rescuing infectious virus, comprising co-transfecting the BAC of claim 35, and a plasmid containing the virus concatemer junction into mammalian cells that are infected with a helper non-replicating virus.

40. The BAC of claim 36, wherein said foreign gene encodes a therapeutic or immunogenic gene product.

41. The BAC of claim 40, wherein said therapeutic or immunogenic gene product is a member selected from the group consisting of a growth factor, hormone, enzyme, vaccine antigen, cytotoxin, immunomodulatory protein, antisense RNA molecule, small interfering RNA, and ribozyme.

* * * * *

UNITED STATES PATENT AND TRADEMARK OFFICE
CERTIFICATE OF CORRECTION

| | | |
|---|---|---|
| PATENT NO. | : 7,494,813 B2 | Page 1 of 1 |
| APPLICATION NO. | : 10/959392 | |
| DATED | : February 24, 2009 | |
| INVENTOR(S) | : Moss et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 453 days Delete the phrase "by 453 days" and insert -- by 938 days --

Signed and Sealed this

Eighteenth Day of May, 2010

David J. Kappos
*Director of the United States Patent and Trademark Office*